United States Patent [19]

Murata et al.

[11] Patent Number: 5,008,456
[45] Date of Patent: Apr. 16, 1991

[54] DIAMINO COMPOUNDS, DINITRO COMPOUNDS, DIOL COMPOUNDS AND A PROCESS FOR PREPARING THE DIAMINO COMPOUNDS

[75] Inventors: Shizuo Murata; Minoru Nakayama, both of Ichihara; Kenji Furukawa, Yokosuka; Ryuji Kobayashi, Yokohama, all of Japan

[73] Assignee: Chisso Corporation, Osaka, Japan

[21] Appl. No.: 433,116

[22] Filed: Nov. 8, 1989

[30] Foreign Application Priority Data

Nov. 9, 1988 [JP] Japan .................. 63-282679

[51] Int. Cl.$^5$ .................................. C07C 211/00
[52] U.S. Cl. ........................... 564/322; 252/299.4; 564/417; 564/418; 564/423; 568/721; 568/931
[58] Field of Search ................ 564/322, 931

[56] References Cited

U.S. PATENT DOCUMENTS 3,247,199 4/1966 Marxer et al. .................. 564/322

OTHER PUBLICATIONS

*Chemical Abstracts*, vol. 111 (16): 144258y (1989).

*Primary Examiner*—Glennon H. Hollrah
*Assistant Examiner*—Scott C. Rand
*Attorney, Agent, or Firm*—Fleit, Jacobson, Cohn, Price, Holman & Stern

[57] ABSTRACT

Diamino compounds, dinitro compounds, diol compounds and a process for preparing the diamino compounds which are useful as materials of poly-imide compounds for obtaining aligning films having high pretilt angles in liquid crystal display elements are provided.

The diamino compounds are represented by the general formula:

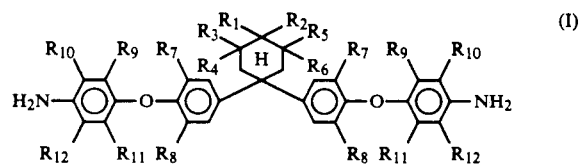

wherein $R_1$–$R_6$ are a hydrogen atom or an alkyl group having 1 to 22 carbon atoms, respectively, and $R_7$–$R_{12}$ are a hydrogen atom, an alkyl group having 1 to 3 carbon atoms, F or Cl respectively.

2 Claims, 10 Drawing Sheets

DIAMINO COMPOUNDS, DINITRO COMPOUNDS, DIOL COMPOUNDS AND A PROCESS FOR PREPARING THE DIAMINO COMPOUNDS

BACKGROUND OF THE INVENTION

The present invention relates to new diamino compounds, dinitro compounds, diol compounds and a process for preparing the diamino compounds. More specifically, the present invention relates to diamino compounds, dinitro compounds, diol compounds and a process for preparing the diamino compounds which are useful as materials of polyimide compounds for obtaining aligning films having high pretilt angles in liquid crystal display elements.

The main current of liquid crystal display elements which are used in conventional clocks, watches and electronic calculators is a twist nematic (abbreviated as TN hereinafter) mode having a structure in which molecular alignment of nematic liquid crystals is twisted at an angle of 90° on the surface of a couple of upper and lower electrode substrates. However, this display mode is insufficient to obtain improved display in quality and size because it shows an indistinct contrast and a narrow viewing angle. In recent years, since a liquid crystal display device using super twisted birefringence effect was reported by T. J. Scheffer and J. Nethriug, Appl. Phys. Lett., 45 (10), 1021 (1984), a liquid crystal display element using supertwist nematic (abbreviated as STN hereinafter) mode in which the molecular alignment of nematic liquid crystals is twisted at angles of 180–290 degrees between the upper and lower electrode substrates has been developed, and then large panel liquid crystal elements having sufficient display quality are developing. In aligning films which are used for these elements, it is required to have a certain angle between the substrate surface and the liquid crystal molecules so as to align the liquid crystal molecules and give a quick response time and secure bistability. Further, it is desirable to give a wide pretilt angle along with a wide twist angle. Among these elements, in an element having a relatively narrow twist angle (twisted at 180–200 degrees), surface treatment on the electrode substrates is sufficiently conducted in the similar manner to those employed in conventional TN cells which are equipped with aligning films having surface alignment of pretilt angles (abbreviated as θ hereinafter) of five degrees and below. However, in STN modes having twist angles of 200–270 degrees along with better display quality, surface alignment having higher pretilt angles (5°<θ<30°) must be used, and therefore liquid crystal display cells having the aligning films which satisfy these angles are required.

In polyimide aligning films which are currently available for the TN mode, the limit of pretilt angles of display cells produced on a industrial scale is about five degrees.

Japanese Publication of Unexamined Patent Application No. 61-240223 describes a liquid crystal display element which is equipped with liquid crystal aligning films produced from a polyimide resin. The resin has a repeating unit represented by a formula:

As materials for the polyimide resin, the only diamine represented by a formula:

is exemplified.

However, the polyimide aligning films produced from the above diamino compound have a problem that high pretilt angles are unobtainable as shown in the comparative examples described hereinafter. Furthermore, there are polyimide aligning films having high pretilt angles for the STN mode. Problems of these films are stability and reproducibility of pretilt angles over the whole display surface of a cell substrate. In order to obtain the high pretilt angles definitely, the best method which is currently conducted is thin film formation by vacuum oblique evaporation of SiO and the like.

However, when the films are mass-produced by the vacuum evaporation, it is a costly process in its production unit. As the result, it is desired earnestly to realize the aligning films having high pretilt angles by the surface treatment of rubbing organic films that is the same method as in the conventional surface treatment method which has been employed in the TN mode.

Moreover, a method for synthesizing bisphenol A as a diol compound is disclosed in U.S. Pat. No. 2,468,982.

SUMMARY OF THE INVENTION

An object of the present invention is to provide new diamino compounds, dinitro compounds, diol compounds and a process for preparing the diamino compounds which are materials for obtaining organic aligning films having excellent aligning properties and uniform high pretilt angles by rubbing treatment.

The present invention is a diamino compound represented by the general formula:

wherein $R_1$-$R_6$ are a hydrogen atom or an alkyl group having 1 to 22 carbon atoms, respectively, and $R_7$-$R_{12}$ are a hydrogen atom, an alkyl group having 1 to 3 carbon atoms, F or Cl respectively.

The present invention is a dinitro compound represented by the general formula:

wherein $R_1$-$R_{12}$ are the same meanings as in the above formula (I).

The present invention is a diol compound represented by the general formula:

wherein at least one of $R_1$-$R_6$ is an alkyl group having 1 to 22 carbon atoms and the others are a hydrogen atom, respectively and $R_7$-$R_8$ are the same meanings as in the above formula (I).

The present invention is a process for preparing diamino compound (I) which comprises reacting diol compound (III) in the presence of a base to obtain dinitro compound (II), and reducing the obtained dinitro compound to produce the diamino compound.

DETAILED DESCRIPTION OF THE INVENTION

Diamino compounds of the present invention include, for instance,
1,1-bis[4-(4-aminophenoxy)-phenyl]cyclohexane,
1,1-bis[4-(4-aminophenoxy)-phenyl]-4-methylclooohexane,
1,1-bis[4-(4-aminophenoxy)-phenyl]-4-ethylcyclohexane,
1,1-bis[4-(4-aminophenoxy)-phenyl]-4-n-propylcyclohexane,
1,1-bis[4-(4-aminophenoxy)-phenyl]-4-n-butylcyclohexane,
1,1-bis[4-(4-aminophenoxy)-phenyl]-4-n-pentylcyclohexane,
1,1-bis[4-(4-aminophenoxy)-phenyl]-4-n-hexylcyclohexane,
1,1-bis[4-(4-aminophenoxy)-phenyl]-4-n-heptylcyclohexane,
1,1-bis[4-(4-aminophenoxy)-phenyl]-4-n-octylcyclohexane,
1,1-bis[4-(4-aminophenoxy)-phenyl]-4-n-nonylcyclohexane,
1,1-bis[4-(4-aminophenoxy)-phenyl]-4-n-decylcyclohexane,
1,1-bis[4-(4-aminophenoxy)-phenyl]-4-n-dodecyccyclohexane,
1,1-bis[4-(4-aminophenoxy)-phenyl]-4-n-dodecylcyclohexane,
1,1-bis[4-(4-aminophenoxy)-phenyl]-4-n-tridecylcyclohexane,
1,1-bis[4-(4-aminophenoxy)-phenyl]-4-n-tetradecylcyclohexane,
1,1-bis[4-(4-aminophenoxy)-phenyl]-4-n-pentadecylcyclohexane,
1,1-bis[4-(4-aminophenoxy)-phenyl]-4-n-hexadecylcyclohexane,
1,1-bis[4-(4-aminophenoxy)-phenyl]-4-n-heptadecylcyclohexane,
1,1-bis[4-(4-aminophenoxy)-phenyl]-4-n-octadecylcyclohexane,
1,1-bis[4-(4-aminophenoxy)-phenyl]-3-methylcyclohexane,
1,1-bis[4-(4-aminophenoxy)-phenyl]-3-ethylcyclohexane,
1,1-bis[4-(4-aminophenoxy)-phenyl]-3-n-propylcyclohexane,
1,1-bis[4-(4-aminophenoxy)-phenyl]-3-n-butylcyclohexane,
1,1-bis[4-(4-aminophenoxy)-phenyl]-3-n-pentylcyclohexane,
1,1-bis[4-(4-aminophenoxy)-phenyl]-3-n-hexylcyclohexane,
1,1-bis[4-(4-aminophenoxy)-phenyl]-3-n-heptylcyclohexane,
1,1-bis[4-(4-aminophenoxy)-phenyl]-3-n-octylcyclohexane,
1,1-bis[4-(4-aminophenoxy)-phenyl]-3-n-nonylcyclohexane,
1,1-bis[4-(4-aminophenoxy)-phenyl]-3-n-decylcyclohexane,
1,1-bis[4-(4-aminophenoxy)-phenyl]-3-n-undecylcyclohexane,
1,1-bis[4-(4-aminophenoxy)-phenyl]-3-n-dodecylcyclohexane,
1,1-bis[4-(4-aminophenoxy)-phenyl]-3-n-tridecylcyclohexane,
1,1-bis[4-(4-aminophenoxy)-phenyl]-3-n-tetradecylcyclohexane,
1,1-bis[4-(4-aminophenoxy)-phenyl]-3-n-pentadecylcyclohexane,
1,1-bis[4-(4-aminophenoxy)-phenyl]-3-n-hexadecylcyclohexane,
1,1-bis[4-(4-aminophenoxy)-phenyl]-3-n-heptadecylcyclohexane,
1,1-bis[4-(4-aminophenoxy)-phenyl]-3-n-octadecylcyclohexane,

1,1-bis[4-(4-aminophenoxy)-3,5-dimethylphenyl]-4-methylcyclohexane,
1,1-bis[4-(4-aminophenoxy)-3,5-dimethylphenyl]-4-ethylcyclohexane,
1,1-bis[4-(4-aminophenoxy)-3,5-dimethylphenyl]-4-npropylcyclohexane,
1,1-bis[4-(4-aminophenoxy)-3,5-dimethylphenyl]-4-n-butylcyclohexane,
1,1-bis[4-(4-aminophenoxy)-3,5-dimethylphenyl]-4-n-pentylcyclohexane,
1,1-bis[4-(4-aminophenoxy)-3,5-dimethylphenyl]-4-n-hexylcyclohexane,
1,1-bis[4-(4-aminophenoxy)-3,5-dimethylphenyl]-4-n-heptylcyclohexane,
1,1-bis[4-(4-aminophenoxy)-3,5-dimethylphenyl]-4-n-octylcyclohexane,
1,1-bis[4-(4-aminophenoxy)-3,5-dimethylphenyl]-4-n-nonylcyclohexane,
1,1-bis[4-(4-aminophenoxy)-3,5-dimethylphenyl]-4-n-decylcyclohexane,
1,1-bis[4-(4-aminophenoxy)-3,5-dimethylphenyl]-4-n-undecylcyclohexane,
1,1-bis[4-(4-aminophenoxy)-3,5-dimethylphenyl]-4-n-dodecylcyclohexane,
1,1-bis[4-(4-aminophenoxy)-3,5-dimethylphenyl]-4-n-tridecylcyclohexane,
1,1-bis[4-(4-aminophenoxy)-3,5-dimethylphenyl]-4-n-tetradecylcyclohexane,
1,1-bis[4-(4-aminophenoxy)-3,5-dimethylphenyl]-4-n-pentadecylcyclohexane,
1,1-bis[4-(4-aminophenoxy)-3,5-dimethylphenyl]-4-n-hexadecylcyclohexane,
1,1-bis[4-(4-aminophenoxy)-3,5-dimethylphenyl]-4-n-heptadecylcyclohexane,
1,1-bis[4-(4-aminophenoxy)-3,5-dimethylphenyl]-4-n-octadecylcyclohexane,
1,1-bis[4-(4-aminophenoxy)-3,5-dimethylphenyl]-3-methylcyclohexane,
1,1-bis[4-(4-aminophenoxy)-3,5-dimethylphenyl]-3-ethylcyclohexane,
1,1-bis[4-(4-aminophenoxy)-3,5-dimethylphenyl]-3-n-propylcyclohexane,
1,1-bis[4-(4-aminophenoxy)-3,5-dimethylphenyl]-3-n-butylcyclohexane,
1,1-bis[4-(4-aminophenoxy)-3,5-dimethylphenyl]-3-n-pentylcyclohexane,
1,1-bis[4-(4-aminophenoxy)-3,5-dimethylphenyl]-3-n-hexylcyclohexane,
1,1-bis[4-(4-aminophenoxy)-3,5-dimethylphenyl]-3-n-heptylcyclohexane,
1,1-bis[4-(4-aminophenoxy)-3,5-dimethylphenyl]-3-n-octylcyclohexane,
1,1-bis[4-(4-aminophenoxy)-3,5-dimethylphenyl]-3-n-nonylcyclohexane,
1,1-bis[4-(4-aminophenoxy)-3,5-dimethylphenyl]-3-n-decylcyclohexane,
1,1-bis[4-(4-aminophenoxy)-3,5-dimethylphenyl]-3-n-undecylcyclohexane,
1,1-bis[4-(4-aminophenoxy)-3,5-dimethylphenyl]-3-n-dodecylcyclohexane,
1,1-bis[4-(4-aminophenoxy)-3,5-dimethylphenyl]-3-n-tridecylcyclohexane,
1,1-bis[4-(4-aminophenoxy)-3,5-dimethylphenyl]-3-n-tetradecylcyclohexane,
1,1-bis[4-(4-aminophenoxy)-3,5-dimethylphenyl]-3-n-pentadecylcyclohexane,
1,1-bis[4-(4-aminophenoxy)-3,5-dimethylphenyl]-3-n-hexadecylcyclohexane,
1,1-bis[4-(4-aminophenoxy)-3,5-dimethylphenyl]-3-n-heptadecylcyclohexane,
1,1-bis[4-(4-aminophenoxy)-3,5-dimethylphenyl]-3-n-octadecylcyclohexane and the like.

Dinitro compounds of the present invention include for instance,
1,1-bis[4-(4-nitrophenoxy)-phenyl]cyclohexane,
1,1-bis[4-(4-nitrophenoxy)-phenyl]-4-methylcyclohexane,
1,1-bis[4-(4-nitrophenoxy)-phenyl]-4-ethylcyclohexane,
1,1-bis[4-(4-nitrophenoxy)-phenyl]-4-n-propylcyclohexane,
1,1-bis[4-(4-nitrophenoxy)-phenyl]-4-n-butylcyclohexane,
1,1-bis[4-(4-nitrophenoxy)-phenyl]-4-n-pentylcyclohexane, and the like.

Diol compounds of the present invention include, for instance,
1,1-bis[4-hydroxyphenyl]-4-methylcyclohexane,
1,1-bis[4-hydroxyphenyl]-4-ethylcyclohexane,
1,1-bis[4-hydroxyphenyl]-4-n-propylcyclohexane,
1,1-bis[4-hydroxyphenyl]-4-n-butylcyclohexane,
1,1-bis[4-hydroxyphenyl]-4-n-pentylcyclohexane,
1,1-bis[4-hydroxyphenyl]-4-n-hexylcyclohexane, and the like.

The diamino compounds of the present invention are mainly used as the raw materials or intermediates of the organic aligning films for the STN display cells. The compounds also can be used for production of high-molecular compounds such as other polyimides, polyamides and the like, and for modification thereof. The compounds also can be used for other objects such as epoxy crosslinkers.

The process for preparing the diamino compounds in the present invention comprises reacting the diol compounds in the presence of a base to obtain the dinitro compounds, and reducing the obtained dinitro compounds. An embodiment of the process is described in the following.

<Production process>

1stage: Cyclohexanone or its derivative and phenol or its derivative (e.g. o-cresol, m-cresol, 2,6-dimethylphenol) are reacted with hydrogen chloride gas in the absence of solvent or in the presence of suitable solvent such as toluene or xylene, and diol compound (III) is obtained.

2nd stage: Diol compound (III) and p-chloronitrobenzene or its derivative (e.g. 5-chloro-2-nitrotoluene) are condensed with KOH or NaOH in a solvent of dimethyl sulfoxide (abbreviated as DMSO hereinafter), and dinitro compound (II) is obtained.

3rd stage: By hydrogen reduction of dinitro compound (II) in a suitable solvent such as toluene, xylene, benzene, ethanol or methanol in the presence of palladium-carbon (abbreviated as Pd-C hereinafter) catalyst at 40°–80° C., diamino compound (I) is obtained.

As shown in the above process, by appropriate selection of $R_1$–$R_6$ and $R_7$–$R_8$ in the first stage, all kinds of desired diol compounds (III) can be prepared selectively, and by appropriate selection of $R_{11}$–$R_{14}$ in the second stage, all kinds of desired dinitro compounds (II) and diamino compounds (I) can be prepared selectively.

The pretilt angles of liquid crystal cells which have aligning films of polyimides prepared from these diamino compounds are mainly influenced by the alkyl chain length of $R_1$–$R_6$, and wider pretilt angles are obtained by longer chain length. The above pretilt angles are also influenced by the rubbing process which is one of the main processes for producing the liquid crystal display elements. Furthermore, pretilt angles may vary in a certain range with other factors such as kinds of liquid crystals employed and preparation conditions of the display elements. For these primary factors, the chain length of $R_1$–$R_6$ of the diamino compounds of the present invention can be selected optionally and the most suitable pretilt angles can be obtained under preparation conditions of the display elements.

When the aligning films of liquid crystal cells are prepared with the diamino compounds of the present invention, various methods for producing common polyimide aligning films are applicable.

An example of an embodiment of the present invention is described in the following.

Using a mixture of 1:1 molar ratio of the diamino compounds of the present invention and tetrabasic acid dianhydride, e. g. pyromellitic dianhydride, the acid dianhydride is ring-opened and added to the diamino group in a suitable solvent at °–20° C. to obtain a polymer. The obtained polyamic acid solution is applied by a Spinner method on a transparent glass substrate of which surface is previously treated with a suitable silane coupling agent. Then, the substrate is heated from 180° to 300° C. and the desired polyimide film usable as the aligning film of the present invention is obtained.

The polyimide compounds prepared from the obtained diamino compounds can realize the high pretilt angles which are necessary to obtain the display elements of the super twist nematic liquid crystals, by the conventional rubbing treatment. It is thought that the high pretilt angles are derived from the cyclohexane rings of diamino compounds of the raw materials and the alkyl groups bonded to the above cyclohexane rings. The diamino compounds of the present invention having such characteristics have been principally designed in order to obtain the intermediates of the raw materials of the organic aligning films for STN. Moreover, these compounds can be used as the raw materials of high polymer compounds of the other polyimides, polyamides and the like and as the modifiers. Furthermore, these compounds can be expected to be used as epoxy crosslinkers and to introduce new properties to high-molecular compounds.

DESCRIPTION OF PREFERRED EMBODIMENTS

The following examples illustrate the compounds of the present invention more specifically, and also the application of polyimide resin obtained from the above compounds to the liquid crystal aligning films is exemplified.

EXAMPLE 1

1st stage 4-n-Propylcyclohexanone 650 g and phenol 1550 g were mixed, and hydrochloric acid gas was blown to the mixture with vigorously stirring at room temperature. The mixture was vigorously stirred for three hours and then left for 50 hours at room temperature. Meantime, the reaction solution was solidified. Warm water 1,000 ml and toluene 3,000 ml were added to the solid. The solid was heated and dissolved completely. The crystals deposited from the solution after cooling were filtered and washed with water and with toluene. After drying the crystals, white crystals 658 g of 1,1-bis(4-hydroxyphenyl)-4-n-propylcyclohexane was obtained by recrystallization from acetone.

Melting point: 171.2°–171.8° C.

2nd stage 1,1-bis(4-hydroxyphenyl)-4-n-propylcyclohexane 179 g obtained by the first stage, KOH 91.4 g and DMSO 500 ml were mixed, and the mixture was heated for one hour at 65° C. and dissolved.

A solution of p-chloronitrobenzene 183 g in DMSO 400 ml was added dropwise at 65° C. to the mixture and allowed to stand for five hours.

After finishing the reaction, the reactant was cooled to room temperature, and toluene 3,000 ml was added. The toluene phase was washed with a 3N-HCl aqueous solution, with a 1N-NaOH aqueous solution and with a saturated salt solution until the washed water became neutral. The toluene solution was dried with $Na_2SO_4$ and chromatographed over alumina with toluene. Toluene was distilled away from the eluted solution. The concentrate was recrystallized from acetone and pale yellow crystals 227.5 g were obtained.

Melting point: 127.3°–127.6° C.

3rd stage After 1,1-bis[4-(4-nitrophenoxy)phenyl]-4-n-propylcyclohexane 112.5 g obtained by the second stage was dissolved in toluene 500 ml and solmix 150 ml, Pd-C catalyst 9.0 g (Pd content: 5% and water content: 55.9%) was added to the solution and the mixture was stirred at 60° C. at ordinary pressure in contact with hydrogen gas. After absorption of hydrogen gas was stopped, the catalyst was filtered off, the filtrate was concentrated. The concentrate was recrystallized from dichloromethane-solmix and pale brown 1,1-bis[4-(4-aminophenoxy)phenyl]-4-n-propylcyclohexane 85.5 g was obtained.

Melting point: 130.5°–131.3° C.

Figure 1:
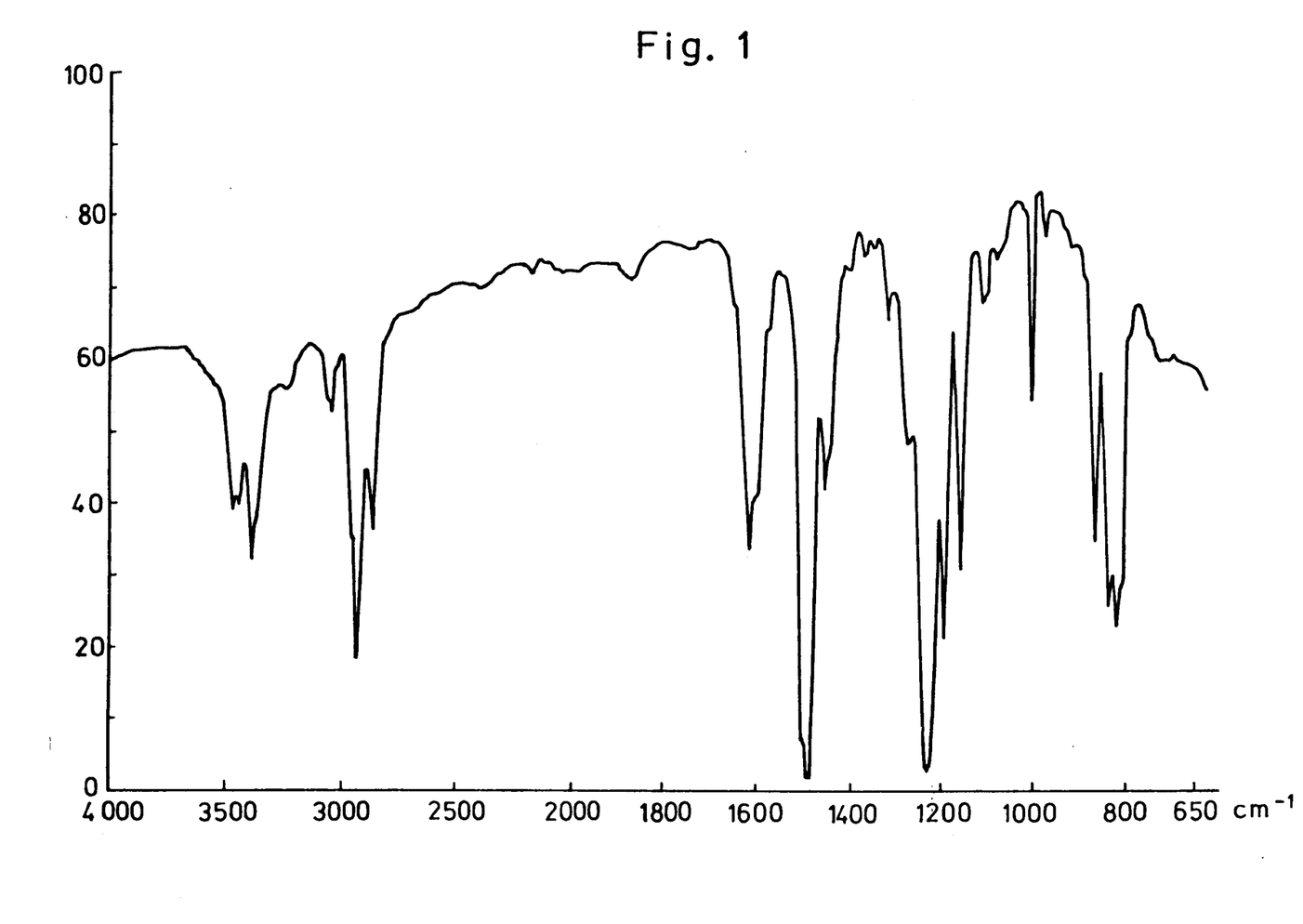
FIGS. 1 and 2 are IR spectrum and $^1$H-NMR spectrum of the diamino compound obtained in Example 1, respectively.
Figure 2:
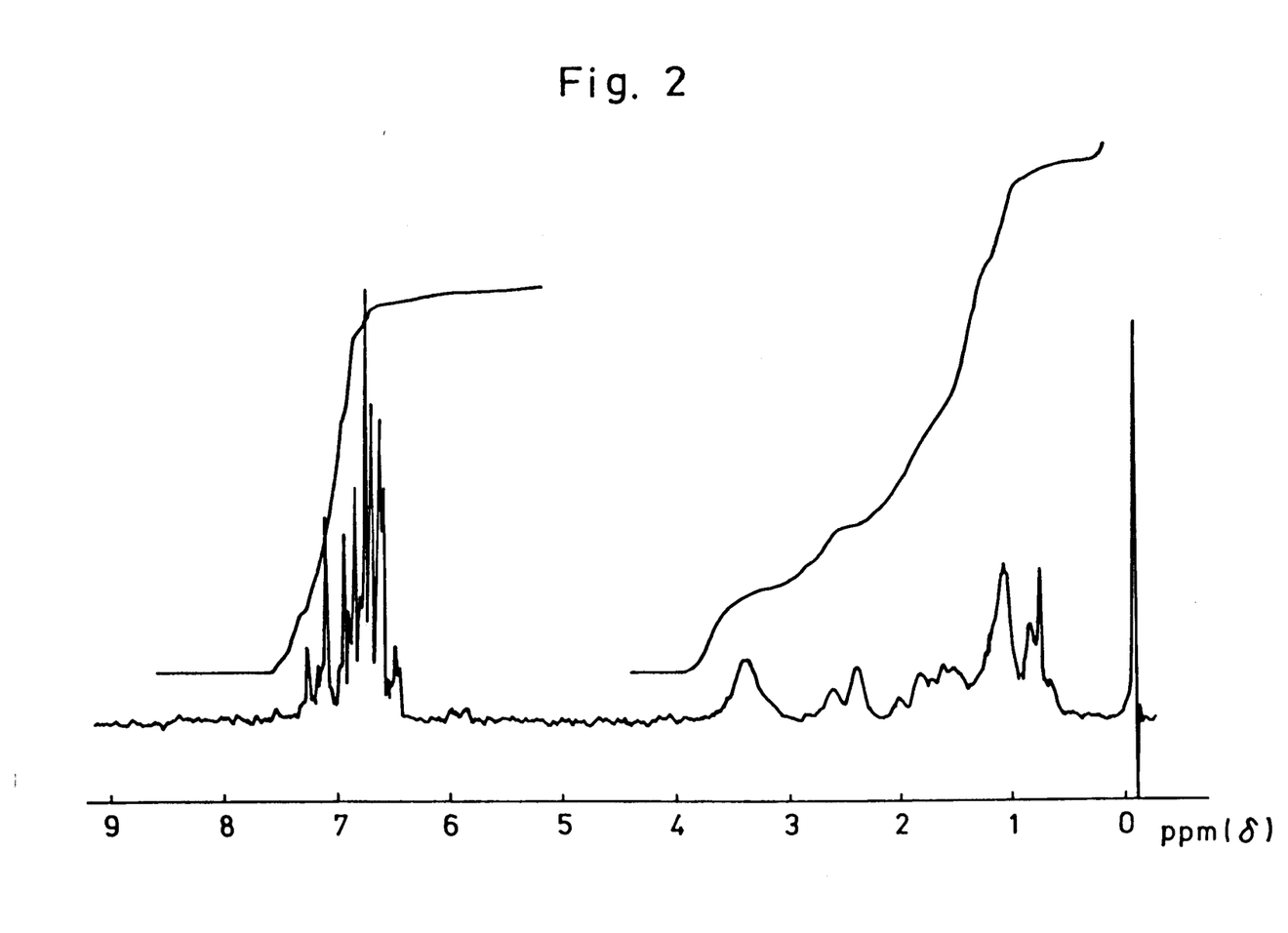

FIGS. 1 and 2 show an infrared (IR) spectrum and a 60 MHz proton nuclear magnetic resonance ($^1$H-NMR) spectrum of the obtained compound, respectively.

EXAMPLE 2

Conditions of operation were the same as described in Example 1 except that the raw material 4-n-propylcyclohexanone was changed to corresponding cyclohexanone derivatives, respectively, and 1,1-bis[4-(4-aminophenoxy)phenyl]cyclohexane, 1,1-bis[4-(4-aminophenoxy)phenyl]-4-ethylcyclohexane and 1,1-bis[4-(4-aminophenoxy)phenyl]-4-n-pentylcyclohexane were prepared.

The melting points of these compounds and their intermediates were as follows.

1,1-bis(4-hydroxyphenyl)cyclohexane
   m.p. = 189.2–189.8° C.   white crystals
1,1-bis[4-(4-nitrophenoxy)phenyl]cyclohexane
   m.p. = 133.8–134.1° C.   pale yellow crystals
1,1-bis[4-(4-aminophenoxy)phenyl]cyclohexane
   m.p. = 155.0–155.5° C.   pale brown crystals
1,1-bis(4-hydroxyphenyl)-4-ethylcyclohexane
   m.p. = 169.5–170.0° C.   white crystals
1,1-bis[4-(4-nitrophenoxy)phenyl]-4-ethylcyclohexane
   m.p. = 134.7–135.4° C.   pale yellow crystals
1,1-bis[4-(4-aminophenoxy)phenyl]-4-ethylcyclohexane
   m.p. = 152.8–153.8° C.   pale brown crystals
1,1-bis(4-hydroxyphenyl)-4-n-pentylcyclohexane
   m.p. = 169.3–169.8° C.   white crystals
1,1-bis[4-(4-nitrophenoxy)phenyl]-4-n-pentylcyclohexane
   m.p. = 93.7–94.0° C.   pale yellow crystals
1,1-bis[4-(4-aminophenoxy)phenyl]-4-n-pentylcyclohexane
   m.p. = 106.4–107.6° C.   pale brown crystals
1,1-bis(4-hydroxyphenyl)-4-methylcyclohexane
   m.p. = 179.8–180.6° C.   white crystals
1,1-bis[4-(4-nitrophenoxy)phenyl]-4-methylcyclohexane
   m.p. = 143.6–144.9° C.   pale yellow crystals -continued

| | |
|---|---|
| 1,1-bis[4-(4-aminophenoxy)phenyl]-4-methylcyclohexane | |
| m.p. = 170.1–170.9° C. | pale brown crystals |
| 1,1-bis(4-hydroxyphenyl)-4-heptylcyclohexane | |
| m.p. = 161.6-163.1° C. | white crystals |
| 1,1-bis[4-(4-nitrophenoxy)phenyl]-4-heptylcyclohexane | |
| | yellow oil |
| 1,1-bis[4-(4-aminophenoxy)phenyl]-4-heptylcyclohexane | |
| m.p. = 125.2-126.7° C. | pale brown crystals | m.p.=125.2°-126.7° C. pale brown crystals

Figure 3:
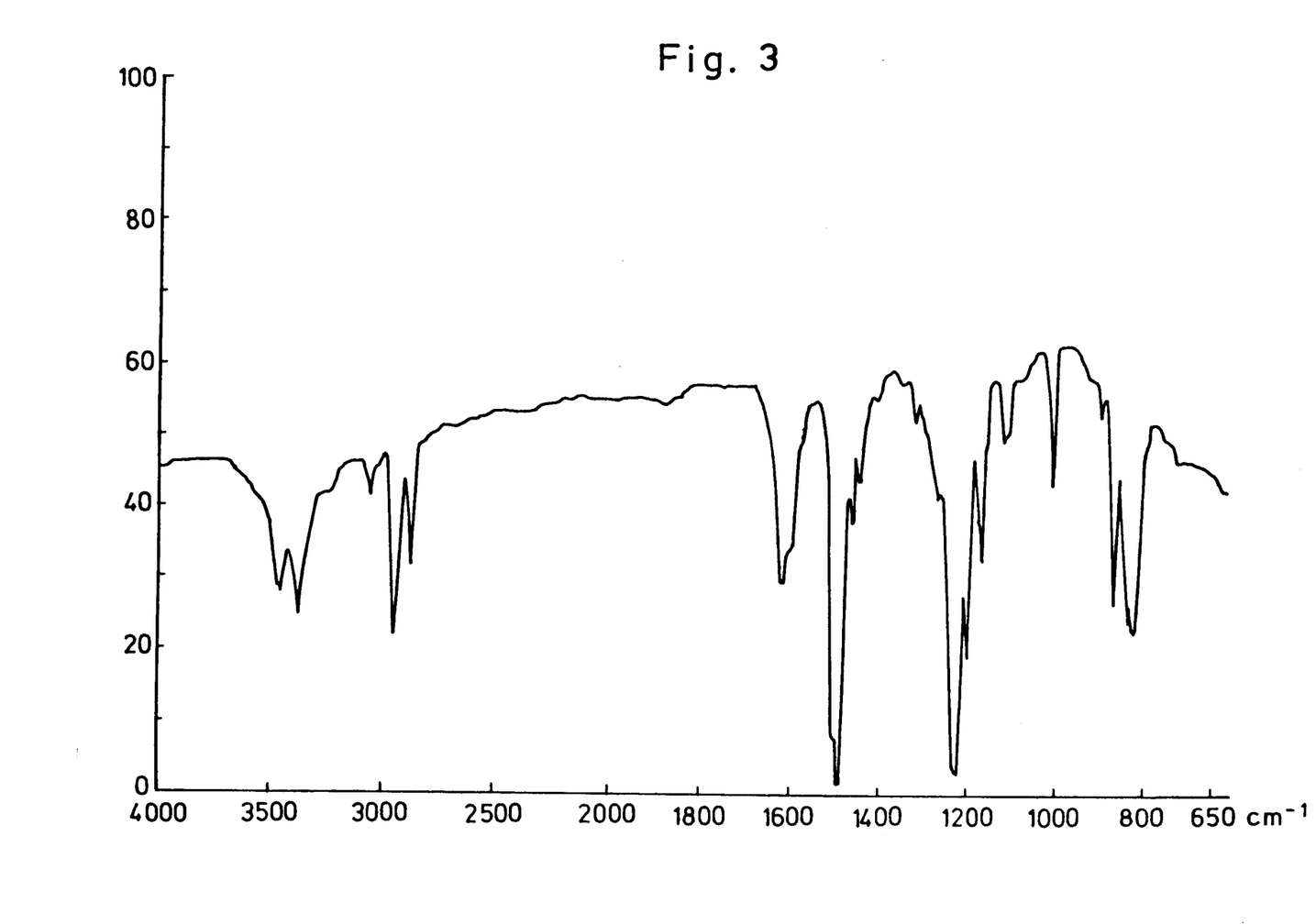
FIGS. 3-10 are IR spectra and $^1$H-NMR spectra of the diamino compound obtained in Example 2.
Figure 4:
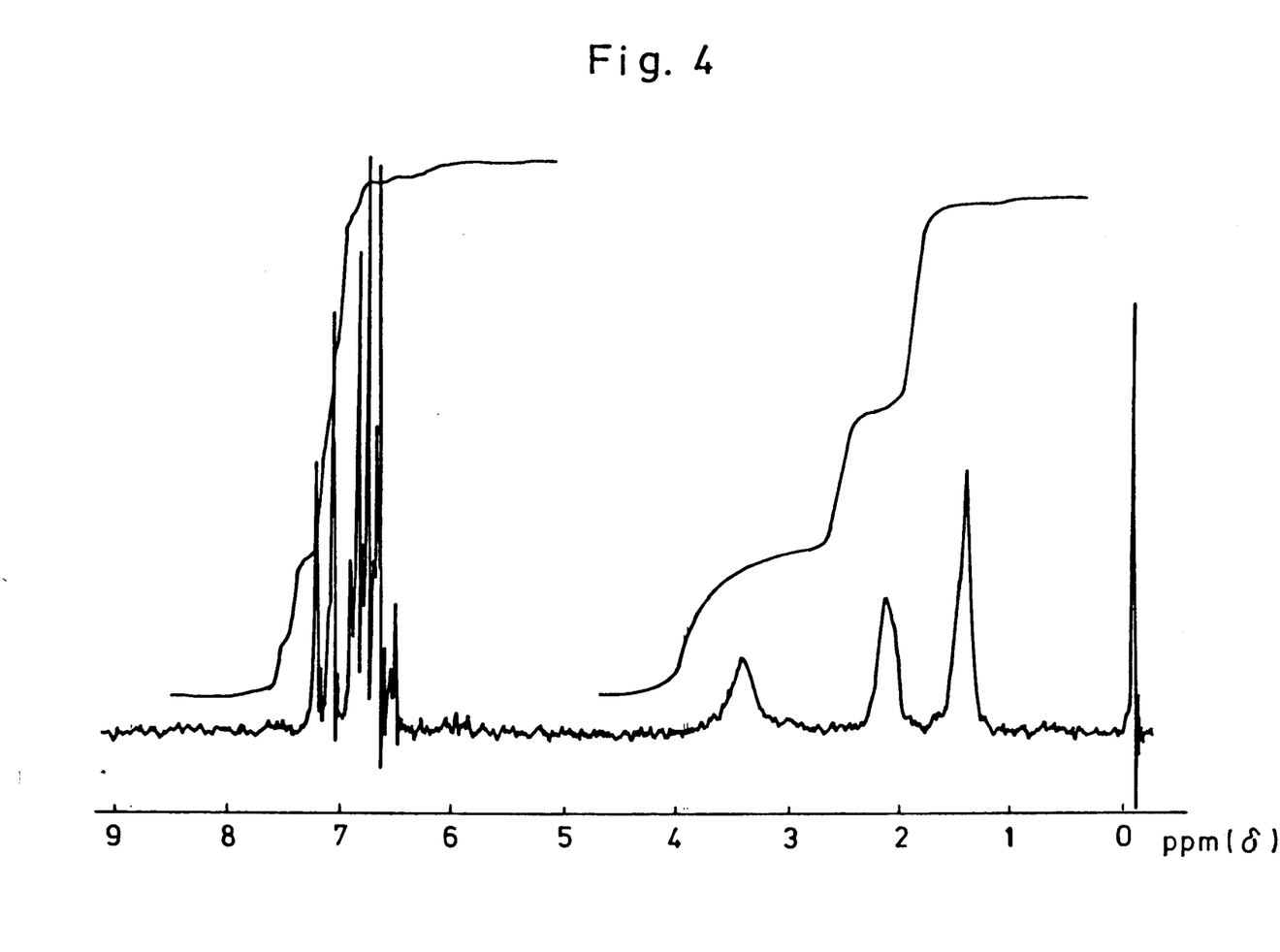
Figure 5:
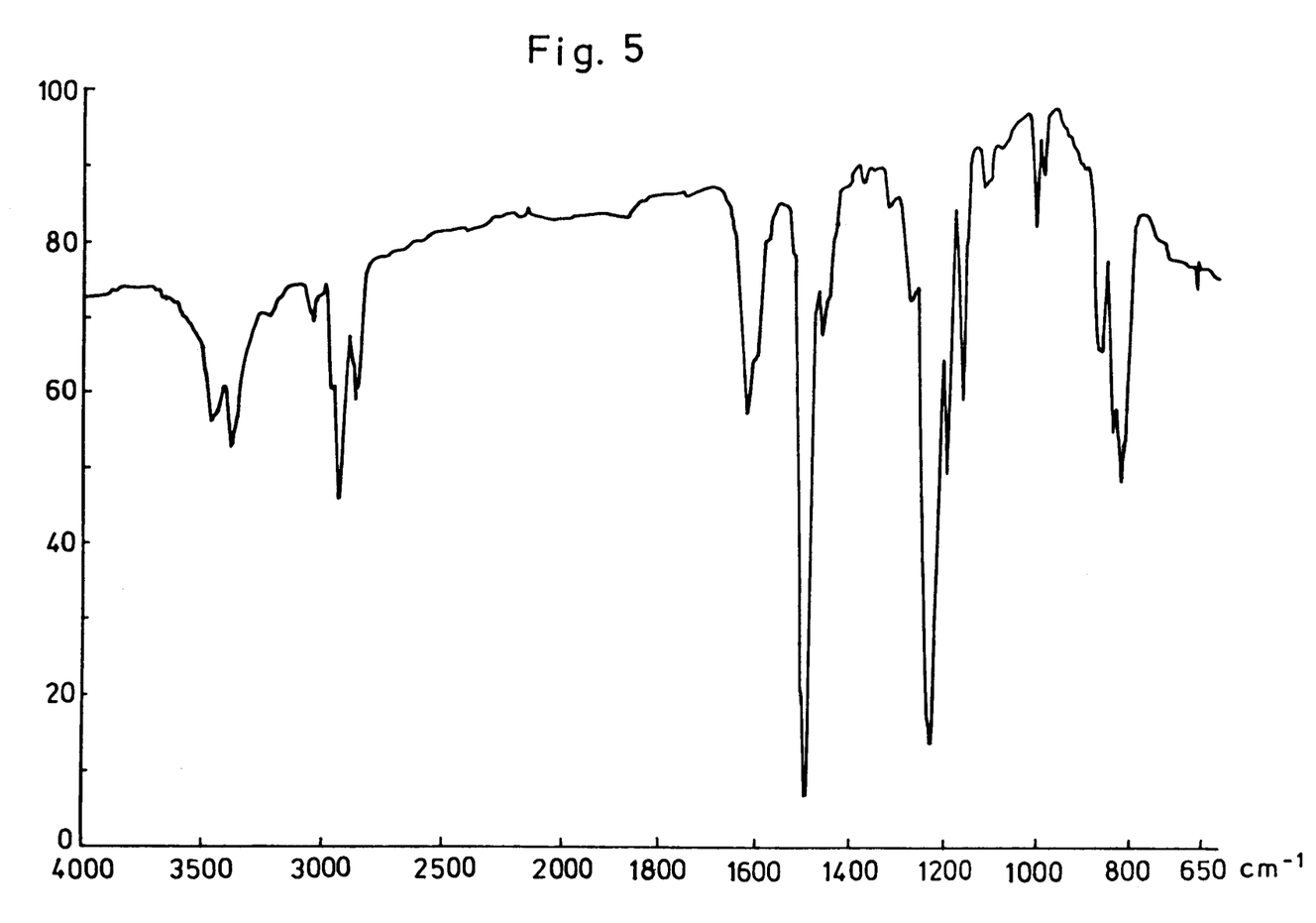
Figure 6:
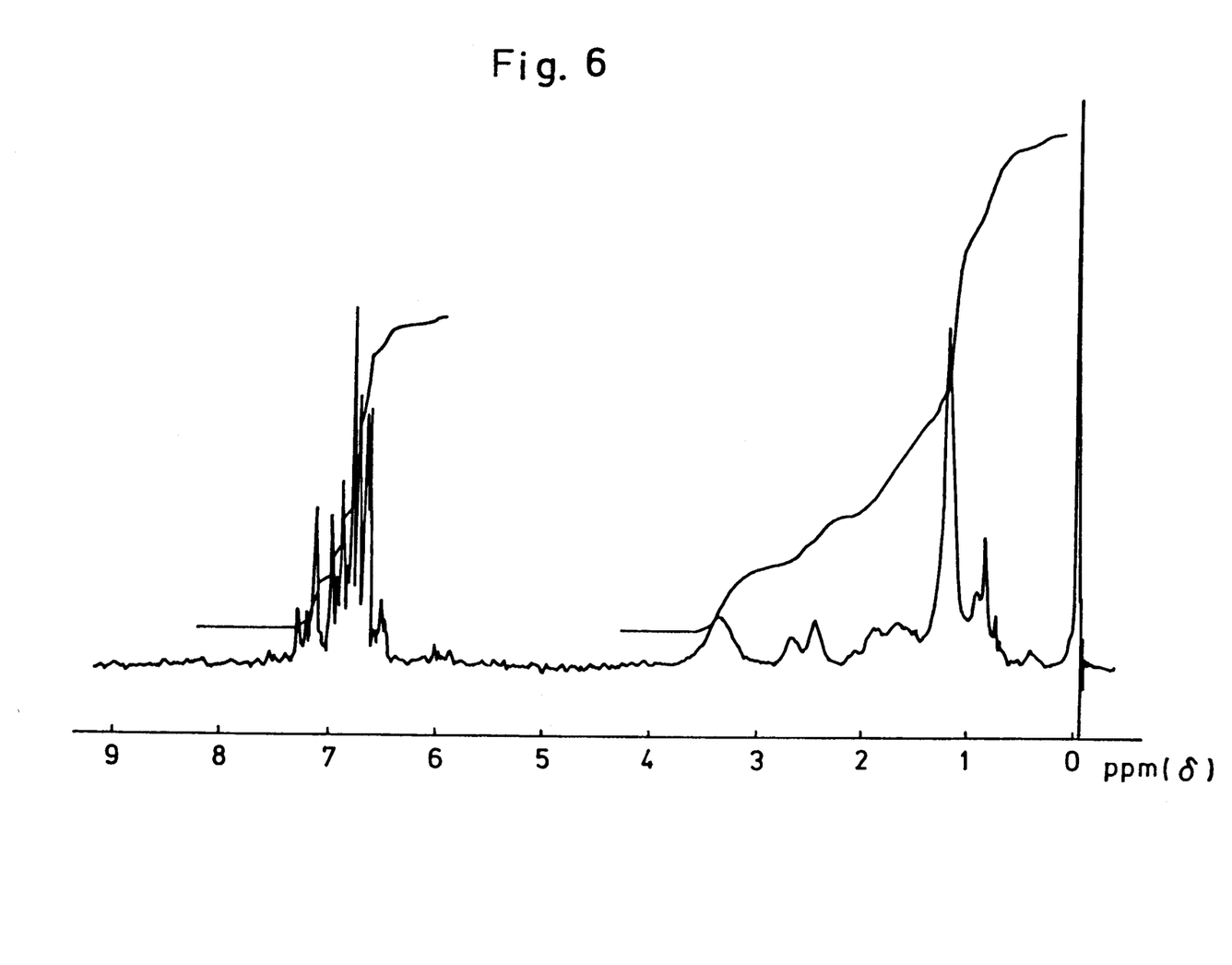
Figure 7:
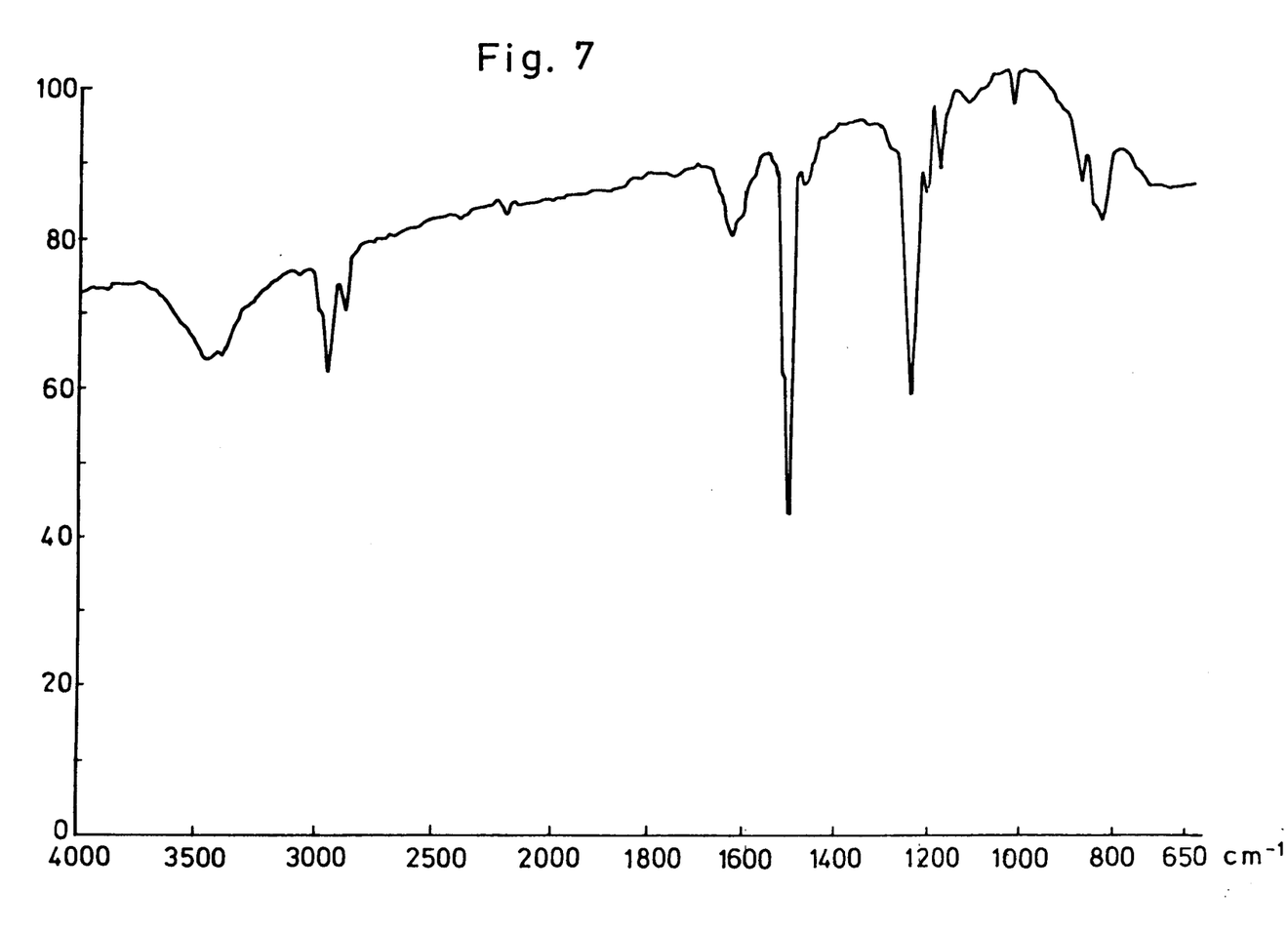
Figure 8:
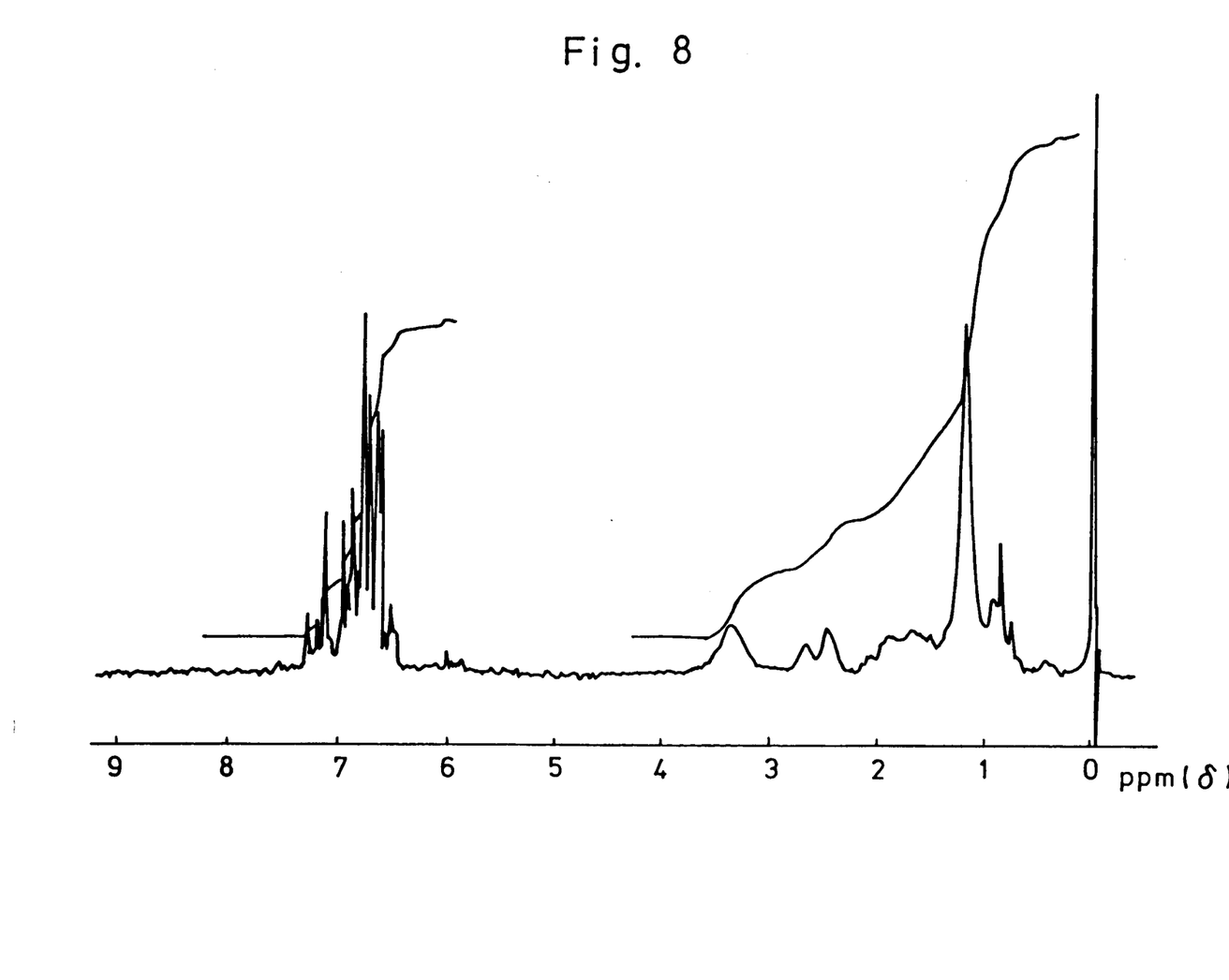
Figure 9:
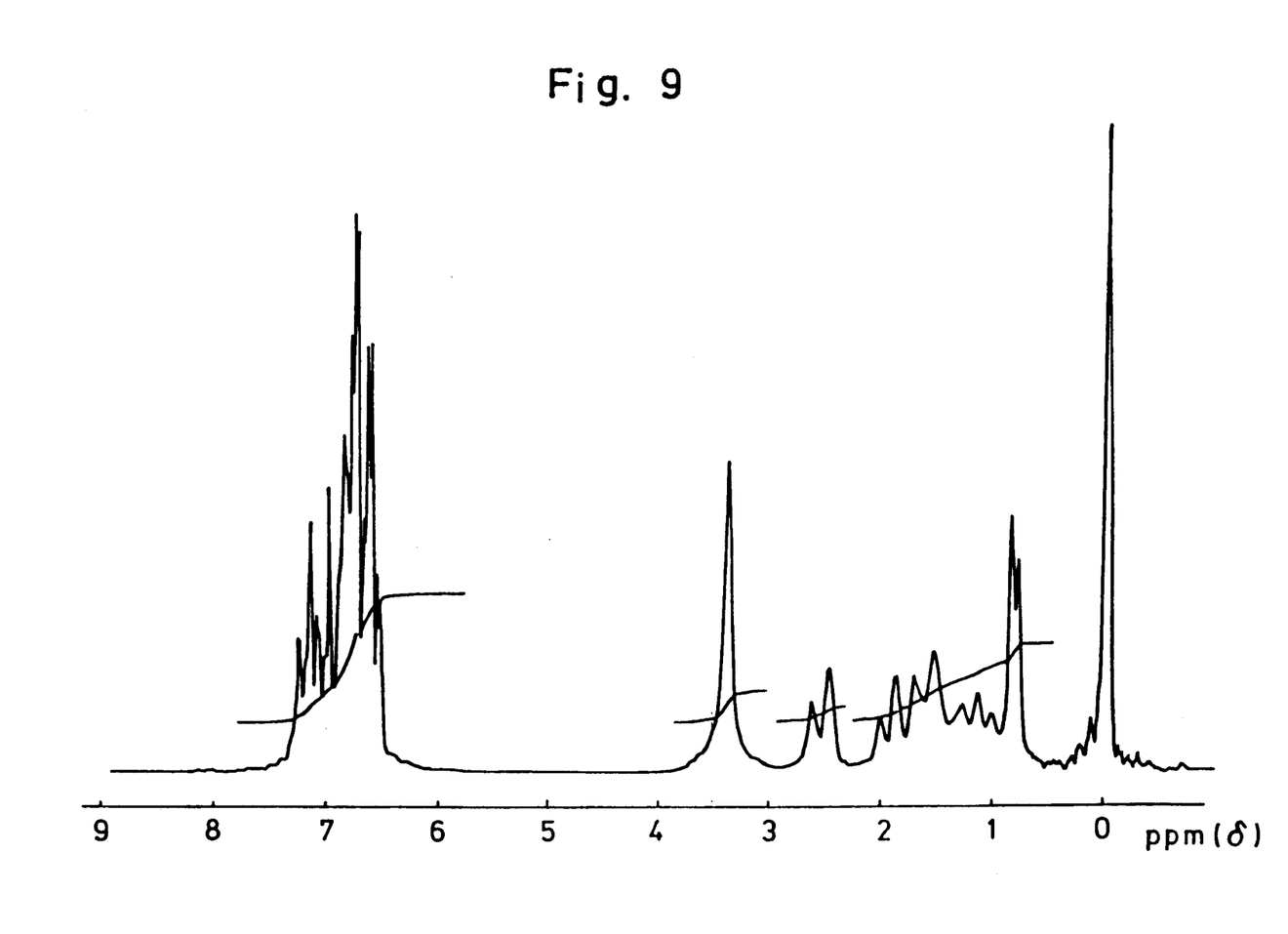
Figure 10:
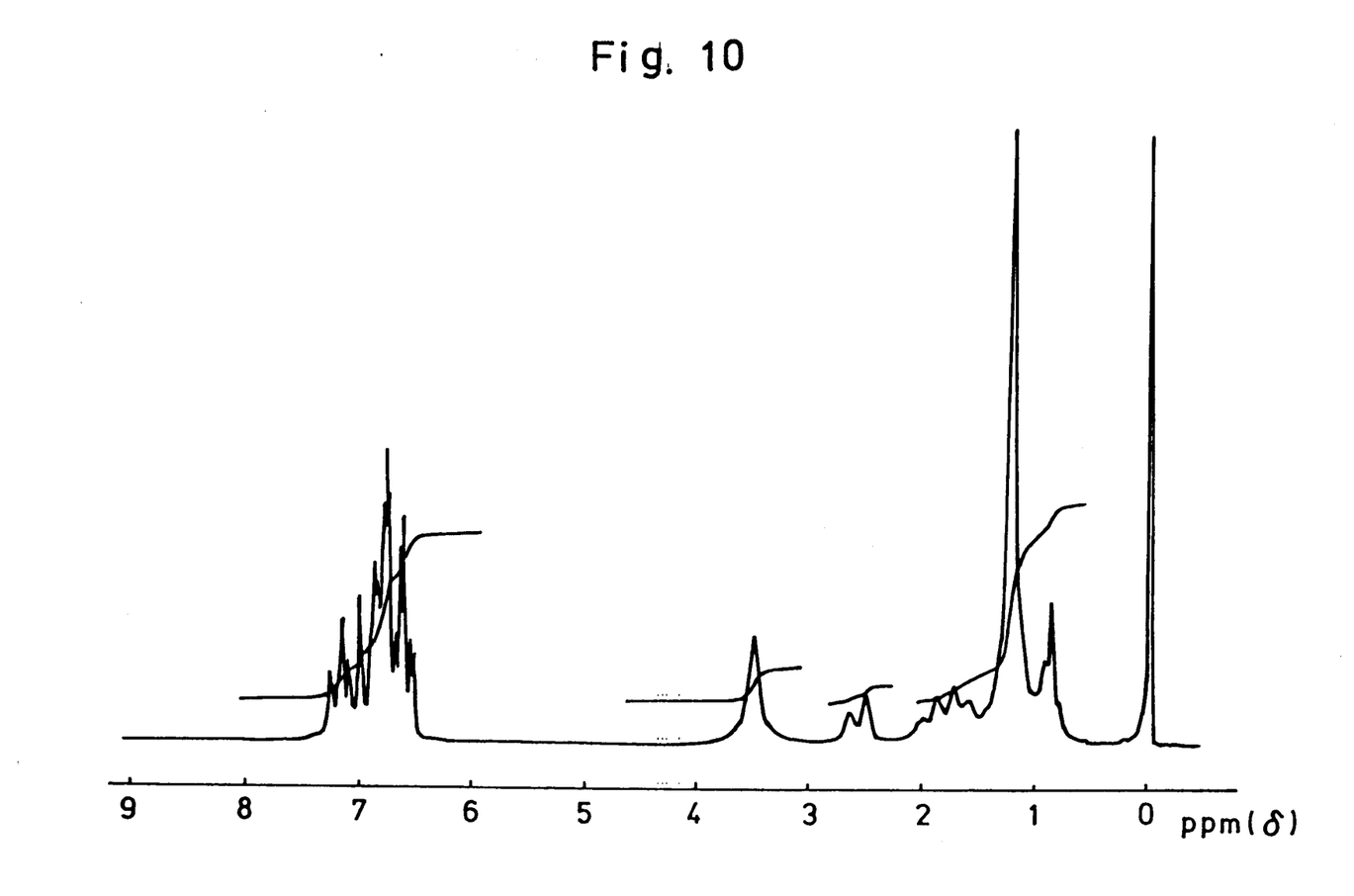

The IR spectra and the NMR spetra of the obtained diamino compounds were shown in FIGS. 3 and 4 (1,1-bis[4-(4-aminophenoxy)phenyl]cyclohexane), in FIGS. 5 and 6 (1,1-bis[4-(4-aminophenoxy)phenyl]-4-ethylcyclohexane), and in FIGS. 7 and 8 (1,1-bis[4-(4-aminophenoxy) phenyl]-4-n-pentylcyclohexane), respectively. Further, the NMR spectra were shown in FIG. 9 (1,1-bis[4-(4-aminophenoxy)phenyl]-4-methylcyclohexane) and in FIG. 10 (1,1-bis[4-(4-aminophenoxy)phenyl]-4-heptylcyclohexane).

APPLICATION EXAMPLE 1

1,1-Bis[4-(4-aminophenoxy)phenyl]-4-n-propylcyclohexane 29.96 g prepared in Example 1, pyro-mellitic dianhydride 15.16 g and para-aminophenyltrimethoxysilane 3.36 g were polymerized in N-methyl-2-pyrrolidone 429 ml at 5°-10° C., and a solution of polyamic acid 10%, $\eta_{20}=221$ cps) was obtained. The obtained solution was diluted with Butyl Cellosolve in concentration 1 to 1 by volume ratio and applied by a rotation coating method (Spinner method) at 3,000 rpm for 20 seconds on transparent grass substrates having transparent electrodes on the one side surface. After the application of the solution, the substrates were preliminarily heated at 100° C. for ten minutes and heated at 200° C. for one hour, and polyimide films having thickness of about 600 Ü were obtained. Further, coated surfaces of two substrates were rubbed with a rubbing apparatus, respectively. A liquid crystal cell having thickness of 10 μm was assembled by the substrates so as to be oriented in parallel and anti parallel rubbing directions and liquid crystal composition YY-4006 made by CHISSO Corporation was sealed in the cell. The aligning properties of the obtained liquid crystal element were excellent and the pretilt angle of the liquid crystal that was measured with the voltage measurement method was 11.8 degrees.

From the above result, by using 1,1-bis[4-(4-aminophenoxy)phenyl]-4-n-propylcyclohexane as one of the raw materials of aligning films, a high value of the pretilt angle can be obtained.

APPLICATION EXAMPLE 2

Using 1,1-bis[4-(4-aminophenoxy)phenyl]cyclohexane, 1,1-bis[4-(4-aminophenoxy)phenyl]-4-ethylcyclohexane and 1,1-bis[4-(4-aminophenoxy)phenyl]-4-n-pentylcyclohexane which are prepared in Example 2, each compound was treated by the same method as in application Example 1, and a 10% solution of polyamic acid was obtained, respectively. The viscosity of each 10% solution of polyamic acid was 179 cps, 113 cps and 122 cps, respectively. Pretilt angles of liquid crystal elements obtained by using the above each solution were 7.3, 9 and 14 degrees, respectively.

From the above result, by lengthening the chain length of the alkyl groups which were bonded to the cyclohexane ring of the raw materials, wider pretilt angles can be obtained, and by selecting the suitable length of the chain, the most suitable values of pretilt angles which are required to produce the liquid crystal element can be obtained.

APPLICATION EXAMPLE 3

Using 1,1-bis[4-aminophenoxy)phenyl]-4-methylcyclohexane and 1,1-bis[4-(4-aminophenoxy)phenyl]-4-heptylcyclohexane which are prepared in Example 2, each compound was treated by the same method as in application Example 1, and a 10% solution of polyamic acid tained, respectively. The viscosity of each 10% solution of polyamic acid was 166 cps and 150 cps, respectively. Pretilt angles of liquid crystal elements obtained by using the above each solution were 8 and 16 degrees, respectively.

COMPARATIVE APPLICATION EXAMPLE

Using the same method as in Applying Examples, a solution of polyamic acid (10%, $\theta_{20}=113$ cps) was obtained from the diamino compound of 2,2-bis[4-(4-aminophenoxy)phenyl]propane. After appliing the solution on the surfaces of substrates, the substrates were preliminarily heated and then heated at a higher temperature, and polyimide films were obtained. Further, these films were rubbed with a rubbing apparatus. A liquid crystal element was assembled by a liquid crystal cell. The pretilt angle of the element that was measured with the voltage measurement method was five degrees.

We claim:

1. A diamino compound represented by the general formula wherein $R_1$–$R_6$ are a hydrogen atom or an alkyl group having 1 to 22 carbon atoms, respectively, and $R_7$–$R_{12}$ are a hydrogen atom, an alkyl group having 1 to 3 carbon atoms, F or Cl, respectively.

2. A dinitro compound represented by the general formula wherein $R_1$–$R_6$ are a hydrogen atom or an alkyl group having 1 to 22 carbon atoms, respectively, and $R_7$–$R_{12}$ are a hydrogen atom, an alkyl group having 1 to 3 carbon atoms, F or Cl, respectively.

* * * * *